United States Patent [19]

Henley et al.

[11] Patent Number: 4,893,626
[45] Date of Patent: Jan. 16, 1990

[54] ELECTRODE FOR ELECTROTHERAPY, ELECTROSURGERY AND MONITORING

[76] Inventors: Ernest J. Henley; William Price, both of 10518 Kinghurst, Houston, Tex. 77099

[21] Appl. No.: 940,657

[22] Filed: Dec. 11, 1986

[51] Int. Cl.$^4$ ............................ A61B 5/04; A61N 1/04
[52] U.S. Cl. .................................. 128/640; 128/798; 128/802; 156/598
[58] Field of Search ................................ 128/639–641, 128/798, 802, 303.13; 604/20, 290; 156/598

[56] References Cited

U.S. PATENT DOCUMENTS

| | | | |
|---|---|---|---|
| 3,419,006 | 12/1968 | King | 604/290 |
| 4,243,052 | 1/1981 | Bailey | 128/798 |
| 4,391,278 | 7/1983 | Cahalan et al. | 128/640 |
| 4,474,570 | 10/1984 | Ariura et al. | 128/798 X |
| 4,706,680 | 11/1987 | Keusch | 128/640 |

FOREIGN PATENT DOCUMENTS 0049431  3/1982  Japan ................... 128/639

Primary Examiner—Lee S. Cohen

[57] ABSTRACT

A new composition of matter formed between natural rubber and aqueous polyethylene oxide gels, and an improved electrode for use in electrotherapy, electrosurgery or current monitoring. Said electrode comprises a layer of a conductive form of said aqueous gel, a current distribution means, an an insulator of said natural rubber. Due to said new composition of matter the natural rubber insulator layer of said electrode bonds directly to the aqueous conductive gel layer. The electrode remains bonded without drying at its outside edges. This new composition of matter provides sufficient adhesion to maintain the elements of an electrotherpy or monitoring electrode in place during medical procedures. The incorporation of an aqueous gel alleviates the need to employ a non-aqueous gel (which lacks the property of even current distribution) or a conducting lattice to perform the functions of current distribution and form retention.

18 Claims, 1 Drawing Sheet

ELECTRODE FOR ELECTROTHERAPY, ELECTROSURGERY AND MONITORING

BACKGROUND OF THE INVENTION

1. Field of the Invention

This invention relates to devices for transmitting current to or from the body, and more particularly to the electrodes of these devices which are applied to the skin surface. Typical devices which use electrodes for electrotherapy include Transcutaneous Electrical Nerve Stimulator (TENS) devices, interferential current devices, and faradic current devices. Also, this invention applies to monitoring electrodes and electrosurgical return electrodes. Pertinent also are electrodes impregnated with chemical, i.e., electrodes for iontophoreats treatments. Typical devices which use electrodes for monitoring include EEG and EKG machines.

2. Description of Related Art

Transcutaneous Electrical Nerve Stimulator ("TENS") units are used to manage acute pain or chronic intractable pain. Other than the TENS device, the most commonly-used treatments for pain have been drugs and surgery. However, analgesic drugs often are ineffective or have undesirable side effects, including the potential for drug abuse and addiction. In addition, pain surgery has a record of complications and undesirable short term effects.

On the other hand, patients treated with the TENS device have been found to begin ambulation much earlier than previously possible with other treatment methods. In addition, TENS devices have been found to reduce the necessary dosages of analgesic drugs, when these two treatment methods are used together.

Other electrotherapy devices also provide physicians with improved or alternative methods for administering to patients.

Electrotherapy devices typically comprise a source of electrical current attached to an electrode through one or more conducting wires. In some electrotherapy devices, i.e., TENS devices, the electrical current may be pulsed and oscillatory. Monitoring devices typically comprise a system for detecting electrical current attached to a monitoring electrode through one or more conducting wires.

the electrical contact between skin and electrotherapy or monitoring electrodes is made by applying the electrode directly to the skin. In order to achieve electrical contact without injury or discomfort to the patient, electrodes generally comprise a means for current to flow into or out of the electrode, a means for distributing current evenly throughout the electrode, and a means for insulating the outer surface of the conducting elements. The means for current flow into or out of the electrode and the means for distributing the current throughout the electrode are typically imbedded in an organic medium with adhesive properties for skin. For example, electrotherapy electrode media such as agar gels and acrylate polymers have been employed with imbedded stainless steel mesh conducting wire in order to distribute the electrical current throughout the electrode media and thereby apply uniform electrical contact over a specific surface area of skin. The means for insulating the outer surface of the conducting elements typically includes an outer nonconducting layer that insulates the current in these elements.

Because problems may be encountered when attempting to adhere organic materials to water-based polymers, previous attempts to substitute aqueous conducting gels for nonconducting organic gels with imbedded steel mesh in electrodes have been unsuccessful due to the inability to bond the organic nonconducting insulator element to the aqueous gel component. Thus, previous attempts to bond the insulating layer to an aqueous conductive gel layer have produced poor attachments.

Additionally, many forces which tend to pull conducting wires out of electrotherapy or monitoring electrodes arise during the ordinary use of their various medical devices. For reasons outlined above, attempts to create an electrode using aqueous gels with sufficient adhesion to the insulating layer to retain the conducting wires during ordinary use of the device have been unsuccessful. Such previous electrodes have been able to withstand pulling forces of only two pounds or less before the electrode components may dissociate.

For reasons outlined above, previous self-adhering electrotherapy electrodes have employed nonaqueous gels. however, without an imbedded current distribution means as described above, nonaqueous gels fail to distribute current evenly throughout the gel, but instead transmit current to isolated "hot spots." In order to avoid this problem, previous electrodes, such as the Ceptor Stix TENS electrode, manufactured by Neuromedics, Inc. of Clute, Tex., have added a stainless steel lattice to distribute the current more evenly throughout the gel. This lattice had the additional function of maintaining the shape of the gel. however, the inclusion of the stainless steel lattice adds to the material and production costs of the electrode, thereby substantially increasing the cost of using the medical device for treatment of patients.

The need to discover a means for bonding the insulator layer to conductive aqueous gels of electrotherapy and monitoring electrodes resurfaced with the development of the aqueous gel products, Hydrogel and Stratum, by the Nepera Chemical Company, Inc., a subsidiary of Schering, A. G. of West Germany. Hydrogel, otherwise known as "irradiated polyox," is a smooth, uniform aqueous gel-filled polyethylene film comprising about 4% polyethylene and 96% water. Stratum, a form of Hydrogel with about 5% salt added, is an excellent conducting gel. Both Stratum and Hydrogel are adhesive to skin.

Stratum is capable of distributing electrotheraphy electrode current evenly throughout a medium up to two inches on a side which easily maintains its geometric form.

Previous attempts to use Stratum as an aqueous conducting gel in electrotherapy electrodes have not produced acceptable results due to the inability to bond the electrode insulating layer to the aqueous conducting gel layer. Although there has been much experimentation and discussion about how materials adhere to one another, the forces responsible for adhesion are not well understood. At one time, adhesion was believed to comprise a mechanical attachment wherein the liquid adhesive occupied cavities in the adherend where it hardened and was thus mechanically anchored somewhat below the surface of the adherend. This type of adhesion is commonly referred to as mechanical adhesion. Although mechanical adhesion may contribute a minor component to adhesive forces in some porous adherends, it is now generally considered that actual adhesive forces are due to primary and secondary valence interactions similar to those that hold the atoms and molecules of the adherents themselves together. This type of adhesion is referred to herein as chemical adhesion.

At one time, chemical adhesion was believed to arise when polar adhesives bonded to polar adherends or nonpolar adhesives bonded to nonpolar adherends, but that polar and nonpolar materials were not capable of bonding through adhesive forces. To the extent that many organic substances are substantially less polar than water, this hypothesis suggests that it may be difficult to adhere an organic insulating layer to an aqueous conducting gel of an electrotherapy electrode, except, perhaps, by means of mechanical adhesion. however, the hypothesis has little predictive value in practice since no adequate means existed for determining polarity. In fact, numerous exceptions were noted when dipole moments were taken as the measure of polarity.

Modern theories of the nature of adhesion require actual wetting of the adherend by the adhesive to achieve contact within molecular distances. Given close proximity, adhesion occurs if the interfacial boundary energy of the adhesive and the adherend is less than the sum of the surface energies of the adhesive and of the adherend. Empirical tests of this hypothesis are difficult to conduct because adequate means of measuring these energies for adhesives and adherends are usually lacking. however, a theoretical basis for the nature of adhesive forces based on general physical and chemical principles have been developed. The emerging view is that adhesive forces are a result of primary and secondary chemical bonds. For example, a review by F. W. Reinhart in *J. Chem. Ed.* 31 128 (March, 1954) suggests that primary bonds in adhesion include electrovalent, covalent, and coordinate covalent bonds involving either the transfer or sharing of electrons among the atoms and molecules of the adhesive and adherend. An example of an electrovalent bond that has been reported in adhesion is the strong bond between copper and sulfur in rubber compounds. An example of a covalent bond in adhesion may be the bond produces by treating glass with a chlorosilane. Coordinate covalent bonds are believed to be important in bonding organic adhesives to materials containing carboxyl or hydroxyl groups, such as cellulose.

Second chemical bonds are the result of van der Waals forces arising from residual energies. Van der Waals forces are stronger in molecules comprising different atoms than in atoms or molecules of the same atom. Van der Waals forces are also stronger in asymmetric molecules that have unequal electron distributions than they are in symmetrical molecules or nearly symmetrical molecules with smaller dipole moments. Van der Waals forces are thought to result from orientation forces of permanent electrical dipole molecules, from induction effects of permanent dipoles on polarizable molecules, and from dispersion forces due to internal electron motions independent of the dipole moments.

Internal stress tests the integrity of adhesive bonds. These internal stresses are the result of faults that may develop within the adhesive layer and vary with the adhesive composition, the bonding conditions, thermal and moisture changes in the adhesive film or in the adherends after bonding, and external loading during use, which in turn will be influenced substantially by the design and geometry of the adhering surface. Since these stresses reduce the theoretical strength of the adhesive bond, the composition of the adhesive and adherend components, the conditions of bonding, moisture content and temperature of the bonded unit, external forces acting on the bonded unit, and the design and geometry of the adhering surfaces are all important considerations in the invention of strongly adhesive components of electrotherapy and monitoring electrodes.

Additionally, electrodes using Stratum gel have a tendency to dry near the edges when the electrode is in use and exposed to air.

SUMMARY OF THE INVENTION

The present invention generally comprises the use of a pure latex natural gum rubber insulator and a conductive aqueous gel such as Stratum to form an electrotherapy or monitoring electrode. One principal element of the present invention is the utilization of natural rubber as an insulator of the electrode current. Unlike other electrotherapy or monitoring device insulators, natural rubber forms strong bonds with conductive aqueous gels such as Stratum. Another principal element of the invention is the ability of the electrode of the present invention to remain adhesive to skin with drying at the edges of the gel substantially retarded.

Figure 1:
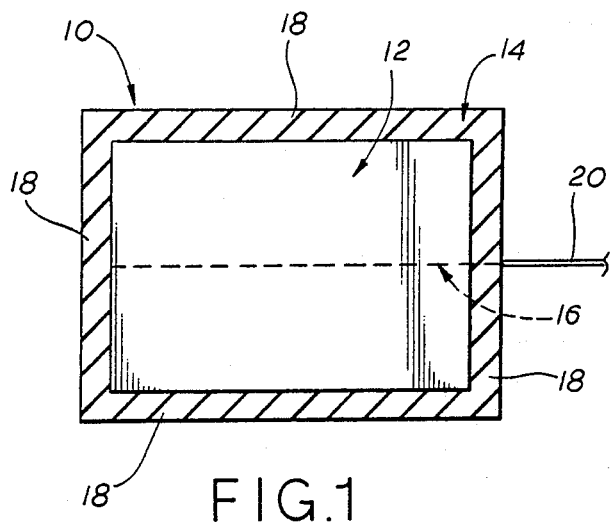
FIG. 1 is a bottom view of one configuration of an electrotherapy or monitoring electrode with a lead wire.

DESCRIPTION OF THE PREFERRED EMBODIMENT(S).

A new composition of matter results when natural rubber (cis 1,4-polyisoprene) contacts aqueous polyethylene oxide gels such as Hydrogel or Stratum. The novel bonding results in a strong adhesion between the organic component and components with extremely high water content.

Experiments illustrated that standard Malaysian rubber is capable of forming strong adhesive bonds with Hydrogel containing 96% water, or with similar formulations of Stratum gel. Vulcanized rubber was not found to react similarly.

As shown in FIGS. 1–4, the electrotherapy or monitoring electrode 10 of the present invention includes a bottom conducting layer 12, a top insulating layer 14, and a conducting means 16 for conducting electrical current to or from said conducting layer. In a preferred embodiment of the present invention said conducting layer 12 is an aqueous gel such as Stratum, said insulating layer 14 is natural rubber, and said layers 12 and 14 are bound together by adhesive interactions between said aqueous gel layer and said natural rubber layer.

Some characteristics and properties of the Nepera Chemical Company, Inc. aqueous conducting gel, Stratum, used in one embodiment of the present invention are listed as follows:

Empirical formula of organic component: $(-CH_2-CH_2-O-)_n-$
Conducting cations: $K^+$ and $Na^+$
wt % of organic component: 4%
wt % of salt: 5%
wt loss on drying: about 90%
typical thickness = 0.06 inches
typical weight = 125 gms/square foot
hardness = 75 to 85
volume resistivity = $1.5 \times 10^3$ ohms/cm
maximum capacitance = 1 microfarad
resistance = 250 ohms (under the conditions of one electrode, room temperature, and from 0 to 1000 hertz)
pH = between 5 and 8 (not buffered)
bioburden < 10 colonies/cm$^3$
irritation index = 0
shelf life = 3 years
temperature range = 0° to 100° C.
functional use = 4 days typical, before rehydration The conducting layer 12 is of sufficient surface area to cover a region of human skin for application or detection of an electrical current in an amount appropriate for an electrotherapy or diagnostic procedure. The conducting layer 12 is of sufficient thickness to conduct said current uniformly and to maintain its own shape when applied and removed from the skin. The dimensions determining the area of insulating layer 14 are sufficiently larger than those determining the area of layer 12 such that overlap 18 of layer 12 by layer 14 exists on all sides of electrode 10. In one preferred embodiment of the present invention the width of overlap 18 is about ⅛ inch.

Figure 4:
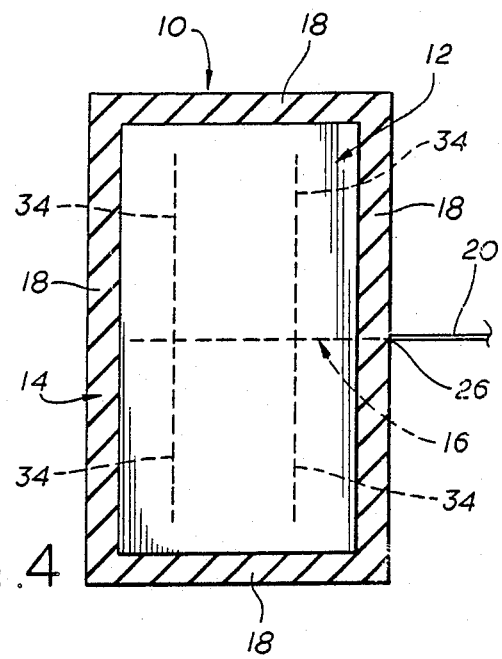
FIG. 4 is a bottom view of a wide electrotheraphy electrode with a bufurcated lead wire.
Figure 2:
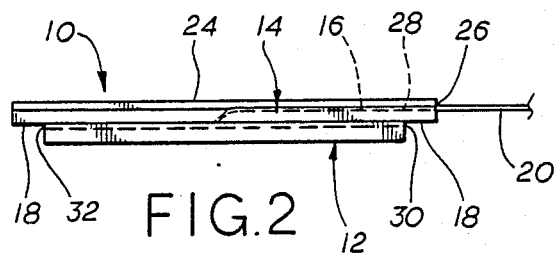
FIG. 2 is a side cross-sectional view of one configuration of an electrotherapy electrode with adhesive backing holding a lead wire in contact with foil.
Figure 5:
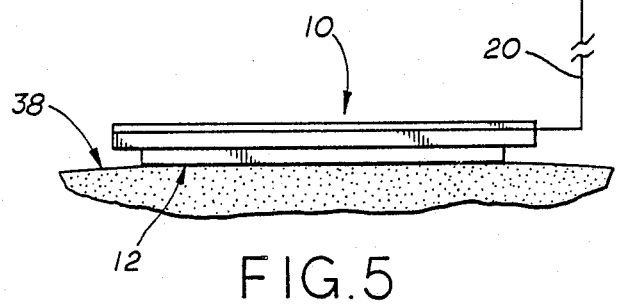
FIG. 5 is a schematic view of an electrotherapy device with a wide electrode resting on skin, and a power source and adhesive tape support.
Figure 3:
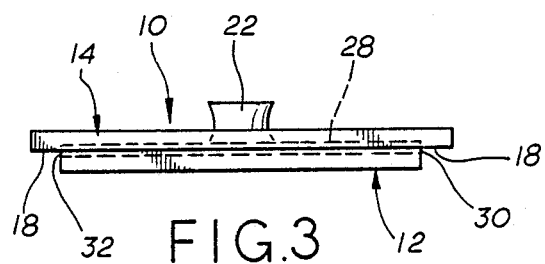
FIG. 3 is a side cross-sectional view of one configuration of a monitoring electrode with a snap connector in contact with foil.
Figure 6:
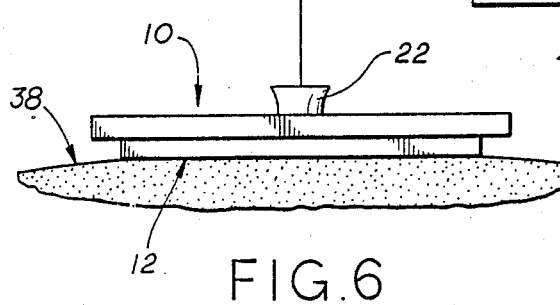
FIG. 6 is a schematic view of a medical device with a monitoring electrode resting on skin, and a current detection means.

As shown in FIGS. 1-6, said current conducting means 16 of electrode 10 may have a lead wire connector or a snap connector at its external terminus. FIGS. 1, 2, 4, and 5, illustrate the use of lead wire connector 20, which may be comprises of steel or copper or some other conducting material; FIGS. 3 and 6 illustrate the use of snap connection 22. As illustrated in FIG. 2, adhesive tape 24 may be used to hold said conducting means in place between layers 12 and 14.

As shown in FIGS. 1-4, said conducting means 16 is embedded in the surface of conducting layer 12 under the contiguous surface of insulating layer 14. In the preferred embodiment of the present invention illustrated in FIG. 1, said conducting means 16 extends from one outer edge 26 of conducting layer 12 into layer 12 under layer 14, but does not extend to the other side of layer 12 or the periphery of layer 14.

when the preferred embodiment of the present invention illustrated in FIG. 1 is used as the electrode for TENS devices, typical electrode dimensions are about 2 inches square.

In the preferred embodiment of the present invention illustrated in FIGS. 2 and 3, foil strip 28, which may be ordinary stainless steel or aluminum foil, is layered between conducting layer 12 and insulating layer 14 and is in electrical contact with conducting means 16. As illustrated in FIGS. 2 and 3, said foil strip 28 may extend from near one outer edge 30 of conducting layer 12 to near the other edge 32 of layer 12, and may be approximately ½ inch wide. The embodiments of the present invention illustrated in FIGS. 2 and 3 are preferred when the length of electrode 10 is greater than about two and a half inches, as for example, in surgical electrodes.

In the preferred embodiment of the present invention illustrated in FIG. 4, conducting means 16 includes one or more branches 34, that extend out to the left and right of conducting means 16. The embodiment of the present invention illustrated in FIG. 4 is preferred when the width of electrode 10 is greater than about two and a half inches.

OPERATION

As shown in FIG. 5, current from an electrical current generator 36 flows through an electrical connection means into electrotherapy electrode 10. In the embodiment of the present invention illustrated in FIG. 5, said connection means is lead wire 20. When conducting layer 12 of electrotherapy electrode 10 is placed directly in contact with skin 38, the current in electrode 10 is distributed evenly across the surface area of conducting layer 12 onto skin 38.

FIG. 6 illustrates the use of a monitoring electrode to detect current on the surface of skin 38. When conducting layer 12 of electrode 10 is placed directly in contact with skin 38, the current on the surface of skin 38 is conducted through electrode 10 to current detection means 40 via an electrical connection means. In the embodiment of the present invention illustrated in FIG. 6, said electrical connection means is snap connector 22.

The natural rubber used in insulator 14 is also known as latex raw rubber, standard Malaysian rubber, gum rubber, natural gum rubber, unvulcanized rubber, and cis-1,4-polyisoprene. The few known commercial applications of natural rubber in its dry state include uses as balloons and surgical gloves. Pure latex natural gum rubber should not be confused with the more familiar material referred to as rubber, which is formed when natural rubber is masticated and combined with vulcanizing agents such as sulfur and other materials, and heated in a vulcanization process.

an important feature of the present invention is that while electrode 10 retains good adhesive properties for skin, the adhesion between conducting layer 12 and insulating layer 14 remains even stronger. This feature is critical, because the electrodes are frequently moved or reused.

Another important feature of the present invention is that conducting layer 12 tends to remain moist and retain its adhesive properties for skin even at its edges. Gel layers not protected by insulating layer overlap 18 dry out more quickly when in use.

In the preferred embodiments of the present invention, adhesion between the aqueous and organic layers of electrode 10 occurs due to the strong bonding between aqueous gel layer 12 and natural rubber insulating layer 14. Uniform current distribution is achieved in the aqueous conducting media and transferred evenly to the surface of skin 38 of the patient at the site where the conducting layer adheres to the skin surface. As illustrated in FIGS. 2 and 3, conducting means 16 in electrical contact with foil strip 28 are preferred for electrodes that are longer than about two and a half inches. As illustrated in FIG. 4, conducting means 16 with branching 34 are preferred for electrodes that are more than about two and a half inches wide. Additionally, the use of aqueous conducting layer 12 in electrode 10, rather than a gel with inferior conducting properties, obviates the additional costs required by gels with inferior conducting properties which require embedded conducting lattices. Due to the discovery of the strong adhesive bond between aqueous Hydrogels or Stratum gels and pure latex natural gum rubber, electrotherapy or monitoring electrode 10 can withstand forces of up to five pounds. Further, due to the use of overlap 18 of insulating layer 14, aqueous gel layer 12 tends to remain moist and adhesive to skin.

the foregoing disclosure and description of the invention are illustrative and explanatory thereof, and various changes in the size, shape and materials, as well as in the details of the illustrated construction may be made without departing from the spirit of the invention.

I claim:

1. The process of adhesion comprising placing natural rubber in physical contact with an aqueous polyethylene oxide gel.

2. The process of claim 1 where said gel contains 4-20% polyethylene oxide.

3. An electrode for use in medical devices comprising:
   (a) a layer of aqueous conductive gel containing an electrolyte,
   (b) an insulating layer comprised of natural rubber,
   (c) an electrical current distribution or collection means in electrical contact with said aqueous conductive gel situated between said aqueous conductive gel layer and said insulating layer.

4. An electrode as stated in claim 3, where said layer of aqueous conducting gel contains approximately 4-20% polyethylene oxide, 1-10% electrolyte, and 70-95% water.

5. An electrode as stated in claim 3 where said natural rubber insulating layer overlaps the edges of said aqueous conductive gel layer.

6. An electrode as stated in claim 3 where said electrical current distribution or collection means comprises a wire capable of conducting an electrical current.

7. An electrode as stated in claim 6 where said conducting wire is branched.

8. A medical device comprising:
   (a) the electrode in claim 3,
   (b) a means for generating or detecting an electrical current, and
   (c) at least one wire in electrical communication with said electrode and said means for generating or detecting an electrical current.

9. The process of applying a current to a surface of skin comprising:
   (a) transmitting current from an electrical generator,
   (b) through at least one conducting wire attached to said electrical generator,
   (c) into the distribution means of the electrode in claim 3; and
   (d) applying said electrode to a surface of skin.

10. An electrode for use in medical devices comprising:
    (a) a layer of aqueous polyethylene oxide gel containing an electrolyte,
    (b) an insulating layer adhering to said gel according to the process of claim 1, and
    (c) an electrical current distribution or collection means in electrical contact with said aqueous gel situated between said aqueous gel layer and said insulating layer.

11. An electrode as stated in claim 10 where said insulating layer overlaps the edges of said aqueous polyethylene oxide gel layer.

12. An electrode as stated in claim 10, where said layer of aqueous polyethylene oxide gel contains approximately 4-20% polyethylene oxide, 1-10% electrolyte, and 70-95% water.

13. An electrode as stated in claim 10 where said electrical current distribution or collection means comprises a wire capable of conducting an electrical current.

14. An electrode as stated in claim 13, where said conducting wire is branched.

15. An electrode as stated in claim 10 where said electrical current distribution or collection means comprises a wire capable of conducting an electrical current in electrical contact with a strip of foil capable of conducting an electrical current.

16. A medical device comprising:
    (a) the electrode of claim 10,
    (b) a means for generating or detecting an electrical current, and
    (c) at least one wire in electrical communication with said distribution means of said electrode and with said means for generating an electrical current, or at least one wire in electrical communication with said collection means of said electrode and with said means for detecting an electrical current.

17. The process of applying a current to a surface of skin, comprising:
    (a) transmitting current from an electrical generator,
    (b) through at least one conducting wire attached to said electrical generator,
    (c) into the distribution means of the electrode in claim 10; and
    (d) applying said electrode to a surface of skin.

18. The composition of matter formed between aqueous polyethylene oxide gels and natural rubber when said gels and rubber are in physical contact with one another.

* * * * *